(12) United States Patent
Matusz et al.

(10) Patent No.: US 9,346,774 B2
(45) Date of Patent: May 24, 2016

(54) PROCESS FOR THE START-UP OF AN EPOXIDATION PROCESS, A PROCESS FOR THE PRODUCTION OF ETHYLENE OXIDE, A 1,2-DIOL, A 1,2-DIOL ETHER, A 1,2-CARBONATE, OR AN ALKANOLAMINE

(75) Inventors: Marek Matusz, Houston, TX (US); Paul Michael McAllister, Houston, TX (US)

(73) Assignee: Shell Oil Company, Houston, TX (US)

( * ) Notice: Subject to any disclaimer, the term of this patent is extended or adjusted under 35 U.S.C. 154(b) by 1721 days.

(21) Appl. No.: 12/437,172

(22) Filed: May 7, 2009

(65) Prior Publication Data

US 2009/0281339 A1 Nov. 12, 2009

Related U.S. Application Data

(60) Provisional application No. 61/051,348, filed on May 7, 2008.

(51) Int. Cl.
*C07D 301/03* (2006.01)
*C07D 301/10* (2006.01)

(52) U.S. Cl.
CPC ............. *C07D 301/10* (2013.01); *Y02P 20/142* (2015.11)

(58) Field of Classification Search
CPC ............................ C07D 301/10; C07D 301/03
USPC ......................................................... 549/536
See application file for complete search history.

(56) References Cited

U.S. PATENT DOCUMENTS

| | | | |
|---|---|---|---|
| 1,976,677 A | 10/1934 | Wittwer | 260/106 |
| 2,219,575 A | 10/1940 | McNamee | 260/348 |
| 3,950,507 A | 4/1976 | Kuklina et al. | 423/626 |
| 3,962,136 A | 6/1976 | Nielsen et al. | 252/454 |
| 4,007,135 A | 2/1977 | Hayden et al. | 252/467 |
| 4,097,414 A | 6/1978 | Cavitt | 252/476 |
| 4,102,820 A | 7/1978 | Cavitt | 252/463 |
| 4,206,128 A | 6/1980 | Cavitt | 260/348.34 |
| 4,224,194 A | 9/1980 | Cavitt | 252/476 |
| 4,242,235 A | 12/1980 | Cognion et al. | 252/455 R |
| 4,321,206 A | 3/1982 | Cavitt | 260/348.34 |
| 4,379,134 A | 4/1983 | Weber et al. | 423/626 |
| 4,389,338 A | 6/1983 | Mitsuhata et al. | 252/463 |
| 4,400,559 A | 8/1983 | Bhise | 560/858 |
| 4,410,453 A | 10/1983 | Kiovsky et al. | 502/253 |
| 4,428,863 A | 1/1984 | Fry | 502/8 |
| 4,430,312 A | 2/1984 | Eickmeyer | 423/223 |
| 4,465,754 A | 8/1984 | Kuin et al. | 430/109 |
| 4,508,927 A | 4/1985 | Bhise et al. | 568/858 |
| 4,555,501 A | 11/1985 | Armstrong | 502/243 |
| 4,761,394 A | 8/1988 | Lauritzen | 502/348 |
| 4,766,105 A | 8/1988 | Lauritzen | 502/347 |
| 4,808,738 A | 2/1989 | Lauritzen | 549/536 |
| 4,820,675 A | 4/1989 | Lauritzen | 502/216 |
| 4,822,900 A | 4/1989 | Hayden | 549/534 |
| 4,831,162 A | 5/1989 | Nakajima et al. | 549/534 |
| 4,845,296 A | 7/1989 | Ahmed et al. | 564/477 |
| 4,874,879 A | 10/1989 | Lauritzen et al. | 549/536 |
| 4,908,343 A | 3/1990 | Bhasin | 502/218 |
| 4,916,243 A | 4/1990 | Bhasin et al. | 549/534 |
| 4,939,114 A | 7/1990 | Nojiri et al. | 502/348 |
| 4,994,588 A | 2/1991 | Kapicak et al. | 549/534 |
| 5,051,395 A | 9/1991 | Mitchell et al. | 502/348 |
| 5,063,195 A | 11/1991 | Jin et al. | 502/341 |
| 5,100,859 A | 3/1992 | Gerdes et al. | 502/439 |
| 5,102,848 A | 4/1992 | Soo et al. | 502/218 |
| 5,112,795 A | 5/1992 | Minahan et al. | 502/324 |
| 5,145,658 A | 9/1992 | Chao | 423/232 |
| 5,155,242 A | 10/1992 | Shankar et al. | 549/534 |
| 5,187,140 A | 2/1993 | Thorsteinson et al. | 502/348 |
| 5,374,748 A | 12/1994 | Rizkalla | 549/534 |
| 5,380,697 A | 1/1995 | Matusz et al. | 502/348 |
| 5,380,885 A | 1/1995 | Kemp | 549/536 |
| 5,395,812 A | 3/1995 | Nagase et al. | 502/238 |
| 5,407,888 A | 4/1995 | Herzog et al. | 502/317 |
| 5,418,202 A | 5/1995 | Evans et al. | 502/348 |
| 5,428,202 A | 6/1995 | Rossi | 219/110 |
| 5,444,034 A | 8/1995 | Rizkalla | 502/347 |
| 5,504,052 A | 4/1996 | Rizkalla et al. | 502/347 |
| 5,504,053 A | 4/1996 | Chou et al. | 502/348 |
| 5,597,773 A | 1/1997 | Evans et al. | 502/348 |

(Continued)

FOREIGN PATENT DOCUMENTS

| | | | | |
|---|---|---|---|---|
| CA | 1180538 | 1/1985 | | B01D 53/34 |
| CN | 1080636 | 12/1994 | | C07D 301/10 |

(Continued)

OTHER PUBLICATIONS

Kirk-Othmer's Encyclopedia of Chemical, 3$^{rd}$ edition, vol. 9, 1980, pp. 445-447.
Brunauer, Stephen, Emmett, P.H. and Teller, Edward: "Adsorption of Gases in Multimolecular Layers", Journal of the American Chemical Society, Feb. 1938, pp. 309-316.
Robert H. Perry, et al., Perry's Chemical Engineers Handbook, 6$^{th}$ Ed., pp. 14-20 to 20-51 (1984).
Beilstein Institute for Organic Chemistry, Frankfurt-Main, DE XP002296657, J. Am. Chem. Society, vol. 56, (1934) pp. 1870-1872.
J. M. Kobe et al., Encyclopedia of Catalysis, vol. 3, I'T. Korrath (Ed.), p. 246, published Dec. 2002, Intercom Araticle, p. 22, Apr. 2002, Workshop on Saftey at SNR—Forum: US100 Years Shell Pernis (English translation provided).

*Primary Examiner* — T. Victor Oh

(57) ABSTRACT

A process is provided for the start-up of an ethylene epoxidation process comprising: (a) contacting a catalyst bed comprising a high selectivity epoxidation catalyst with a feed comprising ethylene, oxygen and an organic chloride for a period of time until an increase of at least $1 \times 10^{-5}$ mole-% of vinyl chloride (calculated as the moles of vinyl chloride relative to the total gas mixture), preferably $2 \times 10^{-5}$ mole-% of vinyl chloride is detected in a reactor outlet gas or a recycle gas loop; and (b) subsequently adjusting the quantity of organic chloride in the feed to a value sufficient to produce ethylene oxide at a substantially optimum selectivity.

14 Claims, No Drawings

(56) References Cited

U.S. PATENT DOCUMENTS

| | | | |
|---|---|---|---|
| 5,646,087 A | 7/1997 | Rizkalla et al. | 502/347 |
| 5,703,253 A | 12/1997 | Evans et al. | 549/536 |
| 5,705,661 A | 1/1998 | Iwakura et al. | 549/536 |
| 5,736,483 A | 4/1998 | Rizkalla | 502/347 |
| 5,739,075 A | 4/1998 | Matusz | 502/302 |
| 5,770,746 A | 6/1998 | Cooker et al. | 549/534 |
| 5,780,656 A | 7/1998 | Rizkalla et al. | 549/534 |
| 5,801,259 A | 9/1998 | Kowaleski | 549/536 |
| 5,840,932 A | 11/1998 | Evans et al. | 549/512 |
| 5,854,167 A | 12/1998 | Rizkalla et al. | 502/216 |
| 5,856,534 A | 1/1999 | Cooker et al. | 549/534 |
| 5,929,259 A | 7/1999 | Lockemeyer | 549/534 |
| 6,040,467 A | 3/2000 | Papavassiliou et al. | 549/534 |
| 6,080,897 A | 6/2000 | Kawabe | 568/858 |
| 6,087,299 A | 7/2000 | Grub et al. | 502/347 |
| 6,368,998 B1 | 4/2002 | Kockemeyer | 502/347 |
| 6,372,925 B1 | 4/2002 | Evans et al. | 549/536 |
| 6,452,027 B1 | 9/2002 | Billig et al. | 549/538 |
| 6,498,122 B2 | 12/2002 | Nakashiro | 502/347 |
| 6,511,938 B1 | 1/2003 | Liu et al. | 502/347 |
| 6,533,843 B2 | 3/2003 | Billig et al. | 95/172 |
| 6,579,825 B2 | 6/2003 | Lockemeyer | 502/347 |
| 6,600,056 B1 | 7/2003 | Mikawa et al. | 549/534 |
| 6,656,874 B2 | 12/2003 | Lockemeyer | 502/347 |
| 6,750,173 B2 | 6/2004 | Rizkalla et al. | 502/348 |
| 6,762,311 B2 | 7/2004 | Rizkalla et al. | 549/534 |
| 6,908,879 B1 | 6/2005 | Shima et al. | 502/242 |
| 7,102,022 B2 | 9/2006 | Evans et al. | 549/536 |
| 2002/0010094 A1 | 1/2002 | Lockemeyer | 502/439 |
| 2003/0162984 A1 | 8/2003 | Lockemeyer et al. | 549/534 |
| 2003/0191019 A1 | 10/2003 | Rizkalla et al. | 502/243 |
| 2004/0049061 A1 | 3/2004 | Lockemeyer et al. | 549/536 |
| 2004/0110971 A1 | 6/2004 | Evans et al. | 549/534 |
| 2004/0198992 A1 | 10/2004 | Matusz et al. | 549/533 |
| 2005/0222442 A1 | 10/2005 | Lockemeyer | 549/534 |
| 2007/0185339 A1 | 8/2007 | Lu | 549/534 |
| 2007/0225511 A1 | 9/2007 | Bortinger et al. | 549/536 |

FOREIGN PATENT DOCUMENTS

| | | | |
|---|---|---|---|
| EP | 3642 | 8/1979 | C07D 301/10 |
| EP | 0026605 | 4/1981 | E04C 2/34 |
| EP | 0161930 | 11/1985 | C07D 301/10 |
| EP | 0176253 | 4/1986 | C07D 301/10 |
| EP | 0211521 | 8/1987 | B01J 23/66 |
| EP | 0266015 | 8/1988 | B01J 23/68 |
| EP | 0326392 | 8/1989 | C07D 301/10 |
| EP | 0327356 | 8/1989 | C07D 301/10 |
| EP | 0352849 | 1/1990 | C07D 301/10 |
| EP | 352850 | 1/1990 | C07D 301/10 |
| EP | 0226234 | 8/1990 | B01J 3/16 |
| EP | 0448157 | 3/1991 | C07C 31/20 |
| EP | 0425020 | 5/1991 | C07D 301/10 |
| EP | 0480539 | 4/1992 | C07D 301/10 |
| EP | 0496470 | 7/1992 | C07D 301/10 |
| EP | 0557833 | 9/1993 | C07D 301/10 |
| EP | 0567273 | 10/1993 | C07D 301/10 |
| EP | 0393785 | 1/1995 | C07D 301/10 |
| EP | 716884 | 6/1996 | B01J 23/66 |
| EP | 0933130 | 8/1999 | B01J 23/66 |
| EP | 1002575 | 5/2000 | B01J 23/04 |
| EP | 1532125 | 5/2005 | C07D 301/10 |
| GB | 117663 | 7/1918 | |
| GB | 119183 | 9/1918 | |
| GB | 1489335 | 10/1974 | B01J 23/66 |
| GB | 2161480 | 1/1986 | C07D 301/10 |
| JP | 4346835 | 2/1992 | B01J 23/66 |
| SU | 1255200 | 3/1982 | B01J 23/96 |
| WO | WO9505896 | 3/1995 | B01J 23/66 |
| WO | WO9517957 | 7/1995 | B01J 23/68 |
| WO | WO9604989 | 2/1996 | B01J 23/50 |
| WO | WO9623585 | 8/1996 | B01J 23/66 |
| WO | WO9623586 | 8/1996 | B01J 37/00 |
| WO | WO9746317 | 12/1997 | B01J 23/66 |
| WO | WO9845280 | 10/1998 | C07D 301/10 |
| WO | WO9858920 | 12/1998 | C07D 301/10 |
| WO | WO9952883 | 10/1999 | C07D 301/04 |
| WO | WO0015332 | 3/2000 | B01J 23/04 |
| WO | WO0015333 | 3/2000 | B01J 23/50 |
| WO | WO0015334 | 3/2000 | B01J 23/50 |
| WO | WO0015335 | 3/2000 | B01J 23/50 |
| WO | WO0196324 | 12/2001 | C07D 301/00 |
| WO | WO03072246 | 9/2003 | B01J 23/66 |
| WO | WO2004002917 | 1/2004 | C04B 24/26 |
| WO | WO2004002954 | 1/2004 | B01J 37/08 |
| WO | WO2004002971 | 1/2004 | C07D 301/10 |
| WO | WO2004002972 | 1/2004 | C07D 301/10 |
| WO | WO2004078736 | 9/2004 | C07D 301/10 |
| WO | WO2004078737 | 9/2004 | C07D 301/10 |
| WO | WO2004089539 | 10/2004 | B01J 23/68 |
| WO | WO2004092148 | 10/2004 | C07D 301/10 |
| WO | WO2004101141 | 11/2004 | B01J 19/30 |
| WO | WO2005035513 | 4/2005 | C07D 301/10 |
| WO | WO2005097318 | 10/2005 | B01J 23/68 |
| WO | WO2006020718 | 2/2006 | B01J 23/50 |
| WO | WO2006028940 | 3/2006 | B01J 21/04 |
| WO | WO2006102189 | 9/2006 | C07D 301/10 |
| WO | WO2007095453 | 8/2007 | B01J 21/04 |
| WO | WO2007122090 | 11/2007 | |

PROCESS FOR THE START-UP OF AN EPOXIDATION PROCESS, A PROCESS FOR THE PRODUCTION OF ETHYLENE OXIDE, A 1,2-DIOL, A 1,2-DIOL ETHER, A 1,2-CARBONATE, OR AN ALKANOLAMINE

This application claims the benefit of U.S. Provisional Application No. 61/051,348 filed May 7, 2008.

FIELD OF THE INVENTION

The invention relates to a process for the start-up of an ethylene epoxidation process which process employs a silver-based highly selective epoxidation catalyst. The invention also relates to a process for the production of ethylene oxide, a 1,2-diol, a 1,2-diol ether, a 1,2-carbonate, or an alkanolamine, which process includes the start-up method of this invention.

BACKGROUND OF THE INVENTION

The catalytic epoxidation of olefins over silver-based catalysts, yielding the corresponding olefin oxide, has been known for a long time. Conventional silver-based catalysts have provided the olefin oxides with notoriously low selectivity. For example, when using conventional catalysts in the epoxidation of ethylene, the selectivity towards ethylene oxide, expressed as a fraction of the ethylene converted, does not reach values above the 6/7 or 85.7 mole-% limit. Therefore, this limit has long been considered to be the theoretically maximal selectivity of this reaction, based on the stoichiometry of the reaction equation

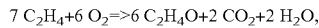

$$7\,C_2H_4 + 6\,O_2 \Rightarrow 6\,C_2H_4O + 2\,CO_2 + 2\,H_2O,$$

cf. Kirk-Othmer's Encyclopedia of Chemical Technology, $3^{rd}$ ed., Vol. 9, 1980, p. 445.

The selectivity determines to a large extent the economical attractiveness of an epoxidation process. For example, an improvement in the selectivity of the epoxidation process can reduce the operating costs of a large-scale ethylene oxide plant by using less olefin to produce the same amount of olefin oxide or increase revenue by producing more olefin oxide from the same amount of olefin.

The olefin oxide produced by the epoxidation process may be reacted with water to form a 1,2-diol, with carbon dioxide to form a 1,2-carbonate, with an alcohol to form a 1,2-diol ether, or with an amine to form an alkanolamine. Thus, 1,2-diols, 1,2-carbonates, 1,2-diol ethers, and alkanolamines may be produced in a multi-step process initially comprising olefin epoxidation and then the conversion of the formed olefin oxide with water, carbon dioxide, an alcohol, or an amine. Any improvement in the epoxidation process can also lead to an improved process for the production of a 1,2-diol, a 1,2-diol ether or an alkanolamine.

Modern silver-based epoxidation catalysts are highly selective towards olefin oxide production. When using the modern catalysts in the epoxidation of ethylene the selectivity towards ethylene oxide can reach values above the 6/7 or 85.7 mole-% limit referred to. An example of such highly selective catalysts is a catalyst comprising silver and a rhenium promoter, cf. for example U.S. Pat. Nos. 4,761,394 and 4,766,105.

A reaction modifier, for example an organic halide, may be added to the feed in an epoxidation process for increasing the selectivity of a highly selective catalyst (cf. for example EP-A-352850, U.S. Pat. Nos. 4,761,394 and 4,766,105, which are herein incorporated by reference). The reaction modifier suppresses the undesirable oxidation of olefin or olefin oxide to carbon dioxide and water, relative to the desired formation of olefin oxide, by a so-far unexplained mechanism. EP-A-352850 teaches that there is an optimum in the selectivity as a function of the quantity of organic halide in the feed, at a constant oxygen conversion level and given set of reaction conditions.

U.S. Pat. No. 7,102,022 B2 relates to the start-up of an epoxidation process wherein a highly selective catalyst is employed. In this document, there is disclosed an improved start-up procedure wherein the highly selective catalyst is subjected to a heat treatment wherein the catalyst is contacted with a feed comprising oxygen at a temperature above the normal operating temperature of the highly selective catalyst (i.e., above 260° C.).

US-A1-2004/0049061 relates to a method of improving the selectivity of a highly selective catalyst having a low silver density. In this document, there is disclosed a method wherein the highly selective catalyst is subjected to a heat treatment which comprises contacting the catalyst with a feed comprising oxygen at a temperature above the normal operating temperature of the highly selective catalyst (i.e., above 250° C.).

U.S. Pat. No. 4,874,879 relates to the start-up of an epoxidation process employing a highly selective catalyst. In this document, there is disclosed an improved start-up procedure wherein the highly selective catalyst is first contacted with a feed containing an organic chloride moderator and ethylene, and optionally a ballast gas, at a temperature below the normal operating temperature of the catalyst.

EP-B1-1532125 relates to the start-up of an epoxidation process wherein a highly selective catalyst is employed. In this document, there is disclosed an improved start-up procedure wherein the highly selective catalyst is first subjected to a pre-soak phase in the presence of a feed containing an organic halide and is then subjected to a stripping phase in the presence of a feed which is free of the organic halide or may comprise the organic halide in a low quantity. The stripping phase is taught to continue for a period of more than 16 hours up to 200 hours.

It goes without saying that there is an economical incentive to shorten the start-up period and make the catalyst operate at a high selectivity with a minimum delay.

DETAILED DESCRIPTION OF THE INVENTION

In accordance with this invention, the start-up of an epoxidation process using a highly selective catalyst can be improved by utilizing the start-up process according to the present invention. The start-up process according to the present invention can reduce the duration of time of the start-up process. Further, within a few hours, the catalyst is able to produce ethylene oxide at or near the selectivity experienced after the catalyst has "lined-out" under normal operating conditions after the start-up process. Because the selectivity of the catalyst quickly increases, there is additional production of ethylene oxide. Further, during the start-up process, there is no longer a need to operate at a catalyst temperature above the catalyst temperature used during normal ethylene oxide production, which may result in an improvement in the lifetime of the catalyst.

Although the present epoxidation process may be carried out in many ways, it is preferred to carry it out as a gas phase process, i.e. a process in which the feed is contacted in the gas phase with the catalyst which is present as a solid material, typically in a packed bed. Generally the process is carried out as a continuous process. The reactor is typically equipped with heat exchange facilities to heat or cool the catalyst. As used herein, the feed is considered to be the composition which is contacted with the catalyst. As used herein, the catalyst temperature or the temperature of the catalyst bed is deemed to be the weight average temperature of the catalyst particles.

When new catalysts as well as aged catalysts which, due to a plant shut-down, have been subjected to a prolonged shut-in period are utilized in the epoxidation process, it may be useful in some instances to pre-treat these catalysts prior to carrying out the start-up process by passing a sweeping gas over the catalyst at an elevated temperature. The sweeping gas is typically an inert gas, for example nitrogen or argon, or mixtures comprising nitrogen and/or argon. The elevated temperature converts a significant portion of organic nitrogen compounds which may have been used in the manufacture of the catalyst to nitrogen containing gases which are swept up in the gas stream and removed from the catalyst. In addition, any moisture may be removed from the catalyst. Typically, when the catalyst is loaded into the reactor, by utilizing the coolant heater, the temperature of the catalyst is brought up to 200 to 250° C., preferably from 210 to 230° C., and the gas flow is passed over the catalyst. Further details on this pre-treatment may be found in U.S. Pat. No. 4,874,879, which is incorporated herein by reference.

The catalyst is subjected to a start-up process which involves an initial step of contacting the catalyst with a feed comprising ethylene, oxygen, and an organic chloride. For the sake of clarity only, this step of the process will be indicated hereinafter by the term "initial start-up phase". During the initial start-up phase, the catalyst is able to produce ethylene oxide at or near the selectivity experienced after the catalyst has "lined-out" under normal initial operating conditions after the start-up process. In particular, during the initial start-up phase, the selectivity may be within 3 mole-%, more in particular within 2 mole-%, most in particular within 1 mole-% of the optimum selectivity performance under normal initial operating conditions. Suitably, the selectivity may reach and be maintained at more than 86.5 mole-%, in particular at least 87 mole-%, more in particular at least 87.5 mole-% during the initial start-up phase. Since the selectivity of the catalyst quickly increases, there is advantageously additional production of ethylene oxide.

In the initial start-up phase, the catalyst is contacted with organic chloride for a period of time until an increase of at least $1 \times 10^{-5}$ mole-% of vinyl chloride (calculated as the moles of vinyl chloride relative to the total gas mixture) is detected in the reactor outlet or the recycle gas loop. Without wishing to be bound by theory, when using organic chlorides other than vinyl chloride, it is believed that the vinyl chloride detected in the outlet or recycle loop is generated by the reaction of surface absorbed chloride on the silver present in the catalyst with a hydrocarbon present in the feed. Preferably, the catalyst is contacted with organic chloride for a period of time until an increase of at least $2 \times 10^{-5}$ mole-% of vinyl chloride, in particular at most $1 \times 10^{-4}$ mole-%, more in particular at most $7.5 \times 10^{-5}$ mole-%, most in particular at most $5 \times 10^{-5}$ mole-% (calculated as the moles of vinyl chloride relative to the total gas mixture) is detected in the reactor outlet or the recycle gas loop. The quantity of organic chloride contacted with the catalyst may be in the range of from 1 to 12 millimolar (mmolar) equivalent of chloride per kilogram of catalyst. The mmolar equivalent of chloride is determined by multiplying the mmoles of the organic chloride by the number of chloride atoms present in the organic chloride molecule, for example 1 mmole of ethylene dichloride provides 2 mmolar equivalent of chloride. The organic chloride may be fed to the catalyst bed for a period of time ranging from 1 to 15 hours, preferably 2 to 10 hours, more preferably from 2.5 to 8 hours. Suitably, the quantity of the organic chloride contacted with the catalyst may be at most 6 mmolar equivalent/kg catalyst, in particular at most 5.5 mmolar equivalent/kg catalyst, more in particular at most 5 mmolar equivalent/kg catalyst. The quantity of the organic chloride in the feed during the initial start-up phase may be at least $1.5 \times 10^{-4}$ mole-%, in particular at least $2 \times 10^{-4}$ mole-%, calculated as moles of chloride, relative to the total feed. The quantity of the organic chloride during the initial start-up phase may be at most 0.1 mole-%, preferably at most 0.01 mole-%, more preferably at most 0.001 mole-%, calculated as moles of chloride, relative to the total feed. Preferably, the initial start-up feed may comprise the organic chloride in a quantity above the optimum quantity used during the initial period of normal ethylene oxide production The feed during the initial start-up phase may also contain additional reaction modifiers which are not organic halides such as nitrate- or nitrite-forming compounds, as described herein.

The feed during the initial start-up phase also contains ethylene. Ethylene may be present in the initial start-up feed in a quantity of at least 10 mole-%, preferably at least 15 mole-%, more preferably at least 20 mole-%, relative to the total feed. Ethylene may be present in the initial start-up feed in a quantity of at most 50 mole-%, preferably at most 45 mole-%, more preferably at most 40 mole-%, relative to the total feed. Preferably, ethylene may be present in the initial start-up feed in the same or substantially the same quantity as utilized during normal ethylene oxide production. This provides an additional advantage in that ethylene concentration does not have to be adjusted between the initial start-up phase and normal ethylene oxide production post start-up making the process more efficient.

The feed during the initial start-up phase also contains oxygen. The oxygen may be present in the initial start-up feed in a quantity of at least 1 mole-%, preferably at least 2 mole-%, more preferably at least 2.5 mole-%, relative to the total feed. The oxygen may be present in the initial start-up feed in a quantity of at most 15 mole-%, preferably at most 10 mole-%, more preferably at most 5 mole-%, relative to the total feed. It may be advantageous to apply a lower oxygen quantity in the initial start-up feed, compared with the feed composition in later stages of the process during normal ethylene oxide production since a lower oxygen quantity in the feed will reduce the oxygen conversion level so that, advantageously, hot spots in the catalyst are better avoided and the process will be more easily controllable.

The feed during the initial start-up phase may also contain carbon dioxide. The carbon dioxide may be present in the initial start-up feed in a quantity of at most 5 mole-%, preferably at most 4 mole-%, relative to the total feed.

In an embodiment, the initial start-up phase also contains less than 2 mole-%, preferably less than 1.5 mole percent, more preferably less than 1.2 mole percent, most preferably less than 1 mole percent, in particular at most 0.75 mole percent carbon dioxide, relative to the total feed. In the normal practice of the present invention, the quantity of carbon dioxide present in the reactor feed is at least 0.1 mole percent, or at least 0.2 mole percent, or at least 0.3 mole percent, relative to the total feed. Suitably, the carbon dioxide may be present in the initial start-up feed in the same or substantially the same quantity as utilized during normal ethylene oxide production.

The balance of the feed during the initial start-up phase may also contain an inert and/or saturated hydrocarbon. The inert and saturated hydrocarbons are described hereinafter.

During the initial start-up phase, the catalyst temperature preferably may be at substantially the same temperature as the normal initial catalyst operating temperature after the epoxidation process has "lined-out" under normal operating conditions after the start-up process. The term "substantially the same temperature" as used herein is meant to include catalyst temperatures within +/−5° C. of the normal initial catalyst operating temperature after the epoxidation process has "lined-out" under normal operating conditions after the start-up process. Preferably, the catalyst temperature is less than 250° C., preferably at most 245° C. The catalyst temperature may be at least 200° C., preferably at least 220° C., more preferably at least 230° C. The reactor inlet pressure may be at most 4000 kPa absolute, preferably at most 3500 kPa absolute, more preferably at most 2500 kPa absolute. The reactor inlet pressure is at least 500 kPa absolute. The Gas Hourly Space Velocity or "GHSV", defined hereinafter, may be in the range of from 500 to 10000 Nl/(l. h).

During the initial start-up phase, the catalyst may first be contacted with a feed comprising ethylene and optionally a saturated hydrocarbon, in particular ethylene and optionally methane. The organic chloride may then be added to the feed. The oxygen may be added to the feed simultaneously with or shortly after the first addition of the organic chloride to the feed. Within a few minutes of the addition of oxygen, the epoxidation reaction can initiate. Carbon dioxide and additional feed components may be added at any time, preferably simultaneously with or shortly after the first addition of oxygen to the initial start-up feed. As discussed above, during the initial start-up phase, the catalyst is able to produce ethylene oxide at or near the selectivity experienced after the catalyst has "lined-out" under normal initial operating conditions after the start-up process. During the initial start-up phase, the catalyst is operated under conditions such that ethylene oxide is produced at a level that is from 45 to 75% of the targeted production level during normal ethylene oxide production, in particular from 50 to 70%, same basis.

Optionally, after the initial start-up phase, the catalyst may be contacted with a feed comprising a reduced quantity of the organic chloride relative to the initial start-up feed. For the sake of clarity only, this step of the process will be indicated hereinafter by the term "intermediate start-up phase". Preferably, the intermediate start-up feed may comprise the organic chloride in a quantity below the optimized quantity used during the initial period of normal ethylene oxide production. For a discussion relating to the optimum quantity of organic chloride see EP-A-352850, U.S. Pat. Nos. 4,761,394 and 4,766,105, which is incorporated herein by reference.

The quantity of organic chloride in the intermediate start-up feed during the intermediate start-up phase may be at most 80% of the quantity in the initial start-up feed, preferably at most 75%, more preferably at most 70% of the quantity of organic chloride in the initial start-up feed. The quantity of organic chloride in the intermediate start-up feed during the intermediate start-up phase may be at least 45% of the quantity in the initial start-up feed, preferably at least 50%, more preferably at least 55% of the quantity of organic chloride in the initial start-up feed. The quantity of the organic chloride in the intermediate start-up feed during the intermediate start-up phase may be more than $1 \times 10^{-4}$ mole-%, in particular at least $1.2 \times 10^{-4}$ mole-%, more in particular at least $1.4 \times 10^{-4}$ mole-%, calculated as moles of chloride, relative to the total feed.

The additional feed components during the intermediate start-up phase may include the components described herein for use in the feed during the initial start-up phase. Preferably, only the quantity of the organic chloride may be decreased and the other components in the feed remain substantially the same as in the initial start-up feed.

During the intermediate start-up phase, the catalyst temperature preferably may be at substantially the same temperature as the normal initial catalyst operating temperature after the epoxidation process has "lined-out" under normal operating conditions after the start-up process. Preferably, the catalyst temperature may be less than 250° C., preferably at most 245° C. The catalyst temperature may be at least 200° C., preferably at least 220° C., more preferably at least 230° C. The reactor inlet pressure may be at most 4000 kPa absolute, preferably at most 3500 kPa absolute, more preferably at most 2500 kPa absolute. The reactor inlet pressure is at least 500 kPa absolute. The Gas Hourly Space Velocity or "GHSV", defined hereinafter, may be in the range of from 500 to 10000 Nl/(l. h) when a gas phase process involving a packed catalyst bed is utilized. The duration of the intermediate start-up phase may be up to 72 hours, in particular from 1 to 36 hours, more in particular from 2 to 24 hours, for example from 3 to 10 hours. During the intermediate start-up phase, the catalyst may be operated under conditions such that ethylene oxide is produced at a level that is from 90 to 100% of the targeted production level during normal ethylene oxide production, in particular from 95 to 100%, same basis.

After the initial start-up phase or optionally after the intermediate start-up phase, the quantity of organic chloride in the feed is adjusted to a value which is practical for the production of ethylene oxide at substantially optimum selectivity, in particular adjusted to a quantity that is within 25% of the optimum quantity of organic chloride that produces the optimum selectivity under normal initial ethylene oxide production conditions, more in particular within 10% of the optimum quantity, and most in particular adjusted to the optimum quantity of organic chloride that produces the optimum selectivity under normal initial ethylene oxide production conditions. For the sake of clarity only, this phase of the epoxidation process, i.e., the phase of the start-up process in which the organic chloride is adjusted to obtain an optimal level of selectivity for normal initial ethylene oxide production, will be indicated herein by the term "start-up adjustment phase".

If the start-up process does not include an intermediate start-up phase, the conditions may be changed during the adjustment phase such that the catalyst is operated under conditions such that ethylene oxide is produced at a level that is from 90 to 100% of the targeted production level during normal ethylene oxide production, in particular from 95 to 100%, same basis.

If the start-up process includes an intermediate start-up phase, the quantity of organic chloride is increased. The increase in the quantity of organic chloride in the feed may be at least $2 \times 10^{-5}$ mole-%, suitably at least $3 \times 10^{-5}$ mole-%, in particular at least $5 \times 10^{-5}$ mole-%, calculated as moles of chloride, relative to the total feed.

The present epoxidation process may be air-based or oxygen-based, see "Kirk-Othmer Encyclopedia of Chemical Technology", $3^{rd}$ edition, Volume 9, 1980, pp. 445-447. In the air-based process, air or air enriched with oxygen is employed as the source of the oxidizing agent while in the oxygen-based processes, high-purity (at least 95 mole-%) or very high purity (at least 99.5 mole-%) oxygen is employed as the source of the oxidizing agent. Reference may be made to U.S. Pat. No. 6,040,467, incorporated by reference, for further description of oxygen-based processes. Presently most epoxidation plants are oxygen-based and this is a preferred embodiment of the present invention.

The organic chloride for use in the present process may be chlorohydrocarbons. Preferably, the organic chloride is selected from the group of methyl chloride, ethyl chloride, ethylene dichloride, vinyl chloride or a mixture thereof. Most preferred reaction modifiers are ethyl chloride, vinyl chloride and ethylene dichloride.

In addition to ethylene, oxygen and the organic chloride, the production feed during the normal epoxidation process may contain one or more optional components, such as nitrogen-containing reaction modifiers, carbon dioxide, inert gases and saturated hydrocarbons.

Nitrogen oxides, organic nitro compounds such as nitromethane, nitroethane, and nitropropane, hydrazine, hydroxylamine or ammonia may be employed as reaction modifiers in the epoxidation process. It is frequently considered that under the operating conditions of ethylene epoxidation the nitrogen containing reaction modifiers are precursors of nitrates or nitrites, i.e. they are so-called nitrate- or nitrite-forming compounds. Reference may be made to EP-A-3642 and U.S. Pat. No. 4,822,900, which are incorporated herein by reference, for further description of nitrogen-containing reaction modifiers.

Suitable nitrogen oxides are of the general formula $NO_x$ wherein x is in the range of from 1 to 2.5, and include for example $NO$, $N_2O_3$, $N_2O_4$, and $N_2O_5$. Suitable organic nitrogen compounds are nitro compounds, nitroso compounds, amines, nitrates and nitrites, for example nitromethane, 1-nitropropane or 2-nitropropane.

Carbon dioxide is a by-product in the epoxidation process. However, carbon dioxide generally has an adverse effect on the catalyst activity, and high concentrations of carbon dioxide are therefore typically avoided. A typical epoxidation reactor feed during the normal epoxidation process may contain a quantity of carbon dioxide in the feed of at most 10 mole-%, relative to the total feed, preferably at most 5 mole-%, relative to the total feed. A quantity of carbon dioxide of less than 3 mole-%, preferably less than 2 mole-%, more preferably less than 1 mole-%, relative to the total feed, may be employed. Under commercial operations, a quantity of carbon dioxide of at least 0.1 mole-%, in particular at least 0.2 mole-%, relative to the total feed, may be present in the feed.

The inert gas may be, for example, nitrogen or argon, or a mixture thereof. Suitable saturated hydrocarbons are propane and cyclopropane, and in particular methane and ethane. Saturated hydrocarbons may be added to the feed in order to increase the oxygen flammability limit.

In the normal ethylene oxide production phase, the invention may be practiced by using methods known in the art of epoxidation processes. For further details of such epoxidation methods reference may be made, for example, to U.S. Pat. Nos. 4,761,394, 4,766,105, 6,372,925 B1, 4,874,879, and 5,155,242, which are incorporated herein by reference In normal ethylene oxide production phase, the process may be carried out using reaction temperatures selected from a wide range. Preferably the reaction temperature is in the range of from 150 to 325° C., more preferably in the range of from 180 to 300° C.

In the normal ethylene oxide production phase, the concentration of the components in the feed may be selected within wide ranges, as described hereinafter.

The quantity of ethylene present in the production feed may be selected within a wide range. The quantity of ethylene present in the feed will be at most 80 mole-%, relative to the total feed. Preferably, it will be in the range of from 0.5 to 70 mole-%, in particular from 1 to 60 mole-%, on the same basis. Preferably, the quantity of ethylene in the production feed is substantially the same as used in the start-up process. If desired, the ethylene concentration may be increased during the lifetime of the catalyst, by which the selectivity may be improved in an operating phase wherein the catalyst has aged, see U.S. Pat. No. 6,372,925 B1 which methods are incorporated herein by reference.

The quantity of oxygen present in the production feed may be selected within a wide range. However, in practice, oxygen is generally applied in a quantity which avoids the flammable regime. The quantity of oxygen applied will be within the range of from 4 to 15 mole-%, more typically from 5 to 12 mole-% of the total feed.

In order to remain outside the flammable regime, the quantity of oxygen present in the feed may be lowered as the quantity of ethylene is increased. The actual safe operating ranges depend, along with the feed composition, also on the reaction conditions such as the reaction temperature and the pressure.

The organic chlorides are generally effective as a reaction modifier when used in small quantities in the production feed, for example up to 0.1 mole-%, calculated as moles of chloride, relative to the total production feed, for example from $0.01 \times 10^{-4}$ to 0.01 mole-%, calculated as moles of chloride, relative to the total production feed. In particular, it is preferred that the organic chloride may be present in the feed in a quantity of from $1 \times 10^{-4}$ to $50 \times 10^{-4}$ mole-%, in particular from $1.5 \times 10^{-4}$ to $25 \times 10^{-4}$ mole-%, more in particular from $1.75 \times 10^{-4}$ to $20 \times 10^{-4}$ mole-%, calculated as moles of chloride, relative to the total production feed. When nitrogen containing reaction modifiers are applied, they may be present in low quantities in the feed, for example up to 0.1 mole-%, calculated as moles of nitrogen, relative to the total production feed, for example from $0.01 \times 10^{-4}$ to 0.01 mole-%, calculated as moles of nitrogen, relative to the total production feed. In particular, it is preferred that the nitrogen containing reaction modifier may be present in the feed in a quantity of from $0.05 \times 10^{-4}$ to $50 \times 10^{-4}$ mole-%, in particular from $0.2 \times 10^{-4}$ to $30 \times 10^{-4}$ mole-%, more in particular from $0.5 \times 10^{-4}$ to $10 \times 10^{-4}$ mole-%, calculated as moles of nitrogen, relative to the total production feed.

Any time during the normal ethylene oxide production phase, the quantity of the organic chloride in the production feed may be adjusted so as to achieve an optimal selectivity towards ethylene oxide formation.

Inert gases, for example nitrogen or argon, may be present in the production feed in a quantity of 0.5 to 90 mole-%, relative to the total feed. In an air based process, inert gas may be present in the production feed in a quantity of from 30 to 90 mole-%, typically from 40 to 80 mole-%. In an oxygen-based process, inert gas may be present in the production feed in a quantity of from 0.5 to 30 mole-%, typically from 1 to 15 mole-%. If saturated hydrocarbons are present, they may be present in a quantity of up to 80 mole-%, relative to the total production feed, in particular up to 75 mole-%, same basis. Frequently they are present in a quantity of at least 30 mole-%, more frequently at least 40 mole-%, same basis.

In the normal ethylene oxide production phase, the epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is a gas phase process involving a packed catalyst bed, the GHSV is in the range of from 1500 to 10000 Nl/(l. h). Preferably, the process is carried out at a work rate in the range of from 0.5 to 10 kmole ethylene oxide produced per $m^3$ of catalyst per hour, in particular 0.7 to 8 kmole ethylene oxide produced per $m^3$ of catalyst per hour, for example 5 kmole ethylene oxide produced per $m^3$ of catalyst per hour. As used herein, the work rate is the amount of ethylene oxide produced per unit volume of catalyst per hour and the selectivity is the molar quantity of ethylene oxide formed relative to the molar quantity of ethylene converted. Suitably, the process is conducted under conditions where ethylene oxide partial pressure in the product mix is in the range of from 5 to 200 kPa, for example 11 kPa, 27 kPa, 56 kPa, 77 kPa, 136 kPa, and 160 kPa. The term "product mix" as used herein is understood to refer to the product recovered from the outlet of an epoxidation reactor.

Generally, the epoxidation catalyst is a supported catalyst. The carrier may be selected from a wide range of materials. Such carrier materials may be natural or artificial inorganic materials and they include silicon carbide, clays, pumice, zeolites, charcoal, and alkaline earth metal carbonates, such as calcium carbonate. Preferred are refractory carrier materials, such as alumina, magnesia, zirconia, silica, and mixtures thereof. The most preferred carrier material is α-alumina.

The surface area of the carrier may suitably be at least 0.1 m$^2$/g, preferably at least 0.3 m$^2$/g, more preferably at least 0.5 m$^2$/g, and in particular at least 0.6 m$^2$/g, relative to the weight of the carrier; and the surface area may suitably be at most 20 m$^2$/g, preferably at most 10 m$^2$/g, more preferably at most 6 m$^2$/g, and in particular at most 4 m$^2$/g, relative to the weight of the carrier. "Surface area" as used herein is understood to relate to the surface area as determined by the B.E.T. (Brunauer, Emmett and Teller) method as described in Journal of the American Chemical Society 60 (1938) pp. 309-316. High surface area carriers, in particular when they are alpha alumina carriers optionally comprising in addition silica, alkali metal and/or alkaline earth metal components, provide improved performance and stability of operation.

The water absorption of the carrier may suitably be at least 0.2 g/g, preferably at least 0.25 g/g, more preferably at least 0.3 g/g, most preferably at least 0.35 g/g; and the water absorption may suitably be at most 0.85 g/g, preferably at most 0.7 g/g, more preferably at most 0.65 g/g, most preferably at most 0.6 g/g. The water absorption of the carrier may be in the range of from 0.2 to 0.85 g/g, preferably in the range of from 0.25 to 0.7 g/g, more preferably from 0.3 to 0.65 g/g, most preferably from 0.42 to 0.52 g/g. A higher water absorption may be in favor in view of a more efficient deposition of the metal and promoters on the carrier by impregnation. However, at a higher water absorption, the carrier, or the catalyst made therefrom, may have lower crush strength. As used herein, water absorption is deemed to have been measured in accordance with ASTM C20, and water absorption is expressed as the weight of the water that can be absorbed into the pores of the carrier, relative to the weight of the carrier.

A carrier may be washed, to remove soluble residues, before deposition of the catalyst ingredients on the carrier. Additionally, the materials used to form the carrier, including the burnout materials, may be washed to remove soluble residues. Such carriers are described in U.S. Pat. No. 6,368,998 and WO-A2-2007/095453, which are incorporated herein by reference. On the other hand, unwashed carriers may also be used successfully. Washing of the carrier generally occurs under conditions effective to remove most of the soluble and/or ionizable materials from the carrier.

The washing liquid may be, for example water, aqueous solutions comprising one or more salts, or aqueous organic diluents. Suitable salts for inclusion in an aqueous solution may include, for example ammonium salts. Suitable ammonium salts may include, for example ammonium nitrate, ammonium oxalate, ammonium fluoride, and ammonium carboxylates, such as ammonium acetate, ammonium citrate, ammonium hydrogencitrate, ammonium formate, ammonium lactate, and ammonium tartrate. Suitable salts may also include other types of nitrates such as alkali metal nitrates, for example lithium nitrate, potassium nitrate and cesium nitrate. Suitable quantities of total salt present in the aqueous solution may be at least 0.001% w, in particular at least 0.005% w, more in particular at least 0.01% w and at most 10% w, in particular at most 1% w, for example 0.03% w. Suitable organic diluents which may or may not be included are, for example, one or more of methanol, ethanol, propanol, isopropanol, tetrahydrofuran, ethylene glycol, ethylene glycol dimethyl ether, diethylene glycol dimethyl ether, dimethylformamide, acetone, or methyl ethyl ketone.

The preparation of the silver catalyst is known in the art and the known methods are applicable to the preparation of the catalyst which may be used in the practice of the present invention. Methods of depositing silver on the carrier include impregnating the carrier or carrier bodies with a silver compound containing cationic silver and/or complexed silver and performing a reduction to form metallic silver particles. For further description of such methods, reference may be made to U.S. Pat. Nos. 5,380,697, 5,739,075, 4,766,105, and 6,368,998, which are incorporated herein by reference. Suitably, silver dispersions, for example silver sols, may be used to deposit silver on the carrier.

The reduction of cationic silver to metallic silver may be accomplished during a step in which the catalyst is dried, so that the reduction as such does not require a separate process step. This may be the case if the silver containing impregnation solution comprises a reducing agent, for example, an oxalate, a lactate or formaldehyde.

Appreciable catalytic activity is obtained by employing a silver content of the catalyst of at least 10 g/kg, relative to the weight of the catalyst. Preferably, the catalyst comprises silver in a quantity of from 10 to 500 g/kg, more preferably from 50 to 450 g/kg, for example 105 g/kg, or 120 g/kg, or 190 g/kg, or 250 g/kg, or 350 g/kg. As used herein, unless otherwise specified, the weight of the catalyst is deemed to be the total weight of the catalyst including the weight of the carrier and catalytic components.

In an embodiment, the catalyst employs a silver content of the catalyst of at least 150 g/kg, relative to the weight of the catalyst. Preferably, the catalyst comprises silver in a quantity of from 150 to 500 g/kg, more preferably from 170 to 450 g/kg, for example 190 g/kg, or 250 g/kg, or 350 g/kg.

The catalyst for use in the present invention additionally comprises a rhenium promoter component. The form in which the rhenium promoter may be deposited onto the carrier is not material to the invention. For example, the rhenium promoter may suitably be provided as an oxide or as an oxyanion, for example, as a rhenate or perrhenate, in salt or acid form.

The rhenium promoter may be present in a quantity of at least 0.01 mmole/kg, preferably at least 0.1 mmole/kg, more preferably at least 0.5 mmole/kg, most preferably at least 1 mmole/kg, in particular at least 1.25 mmole/kg, more in particular at least 1.5 mmole/kg, calculated as the total quantity of the element relative to the weight of the catalyst. The rhenium promoter may be present in a quantity of at most 500 mmole/kg, preferably at most 50 mmole/kg, more preferably at most 10 mmole/kg, calculated as the total quantity of the element relative to the weight of the catalyst.

In an embodiment, the rhenium promoter is present in a quantity of at least 1.75 mmole/kg, preferably at least 2 mmole/kg, calculated as the total quantity of the element relative to the weight of the catalyst. The rhenium promoter may be present in a quantity of at most 15 mmole/kg, preferably at most 10 mmole/kg, more preferably at most 8 mmole/kg, calculated as the total quantity of the element relative to the weight of the catalyst.

In an embodiment, the catalyst may further comprise a potassium promoter deposited on the carrier. The potassium promoter may be deposited in a quantity of at least 0.5 mmole/kg, preferably at least 1 mmole/kg, more preferably at least 1.5 mmole/kg, most preferably at least 1.75 mmole/kg, calculated as the total quantity of the potassium element deposited relative to the weight of the catalyst. The potassium promoter may be deposited in a quantity of at most 20 mmole/kg, preferably at most 15 mmole/kg, more preferably at most 10 mmole/kg, most preferably at most 5 mmole/kg, on the same basis. The potassium promoter may be deposited in a quantity in the range of from 0.5 to 20 mmole/kg, preferably from 1 to 15 mmole/kg, more preferably from 1.5 to 7.5 mmole/kg, most preferably from 1.75 to 5 mmole/kg, on the same basis. A catalyst prepared in accordance with the present invention can exhibit an improvement in selectivity, activity, and/or stability of the catalyst especially when operated under conditions where the reaction feed contains low levels of carbon dioxide.

The catalyst for use in the present invention may additionally comprise a rhenium co-promoter. The rhenium co-promoter may be selected from tungsten, molybdenum, chromium, sulfur, phosphorus, boron, and mixtures thereof.

The rhenium co-promoter may be present in a total quantity of at least 0.1 mmole/kg, more typically at least 0.25 mmole/kg, and preferably at least 0.5 mmole/kg, calculated as the element (i.e. the total of tungsten, chromium, molybdenum, sulfur, phosphorus and/or boron), relative to the weight of the catalyst. The rhenium co-promoter may be present in a total quantity of at most 40 mmole/kg, preferably at most 10 mmole/kg, more preferably at most 5 mmole/kg, on the same basis. The form in which the rhenium co-promoter may be deposited on the carrier is not material to the invention. For example, it may suitably be provided as an oxide or as an oxyanion, for example, as a sulfate, borate or molybdate, in salt or acid form.

In an embodiment, the catalyst contains the rhenium promoter and tungsten in a molar ratio of the rhenium promoter to tungsten of greater than 2, more preferably at least 2.5, most preferably at least 3. The molar ratio of the rhenium promoter to tungsten may be at most 20, preferably at most 15, more preferably at most 10.

In an embodiment, the catalyst comprises the rhenium promoter and additionally a first co-promoter component and a second co-promoter component. The first co-promoter may be selected from sulfur, phosphorus, boron, and mixtures thereof. It is particularly preferred that the first co-promoter comprises, as an element, sulfur. The second co-promoter component may be selected from tungsten, molybdenum, chromium, and mixtures thereof. It is particularly preferred that the second co-promoter component comprises, as an element, tungsten and/or molybdenum, in particular tungsten. The form in which the first co-promoter and second co-promoter components may be deposited onto the carrier is not material to the invention. For example, the first co-promoter and second co-promoter components may suitably be provided as an oxide or as an oxyanion, for example, as a tungstate, molybdate, or sulfate, in salt or acid form.

In this embodiment, the first co-promoter may be present in a total quantity of at least 0.2 mmole/kg, preferably at least 0.3 mmole/kg, more preferably at least 0.5 mmole/kg, most preferably at least 1 mmole/kg, in particular at least 1.5 mmole/kg, more in particular at least 2 mmole/kg, calculated as the total quantity of the element (i.e., the total of sulfur, phosphorus, and/or boron) relative to the weight of the catalyst. The first co-promoter may be present in a total quantity of at most 50 mmole/kg, preferably at most 40 mmole/kg, more preferably at most 30 mmole/kg, most preferably at most 20 mmole/kg, in particular at most 10 mmole/kg, more in particular at most 6 mmole/kg, calculated as the total quantity of the element relative to the weight of the catalyst.

In this embodiment, the second co-promoter component may be present in a total quantity of at least 0.1 mmole/kg, preferably at least 0.15 mmole/kg, more preferably at least 0.2 mmole/kg, most preferably at least 0.25 mmole/kg, in particular at least 0.3 mmole/kg, more in particular at least 0.4 mmole/kg, calculated as the total quantity of the element (i.e., the total of tungsten, molybdenum, and/or chromium) relative to the weight of the catalyst. The second co-promoter may be present in a total quantity of at most 40 mmole/kg, preferably at most 20 mmole/kg, more preferably at most 10 mmole/kg, most preferably at most 5 mmole/kg, calculated as the total quantity of the element relative to the weight of the catalyst.

In an embodiment, the molar ratio of the first co-promoter to the second co-promoter may be greater than 1. In this embodiment, the molar ratio of the first co-promoter to the second co-promoter may preferably be at least 1.25, more preferably at least 1.5, most preferably at least 2, in particular at least 2.5. The molar ratio of the first co-promoter to the second co-promoter may be at most 20, preferably at most 15, more preferably at most 10.

In an embodiment, the molar ratio of the rhenium promoter to the second co-promoter may be greater than 1. In this embodiment, the molar ratio of the rhenium promoter to the second co-promoter may preferably be at least 1.25, more preferably at least 1.5. The molar ratio of the rhenium promoter to the second co-promoter may be at most 20, preferably at most 15, more preferably at most 10.

In an embodiment, the catalyst comprises the rhenium promoter in a quantity of greater than 1 mmole/kg, relative to the weight of the catalyst, and the total quantity of the first co-promoter and the second co-promoter deposited on the carrier may be at most 3.8 mmole/kg, calculated as the total quantity of the elements (i.e., the total of sulfur, phosphorous, boron, tungsten, molybdenum and/or chromium) relative to the weight of the catalyst. In this embodiment, the total quantity of the first co-promoter and the second co-promoter may preferably be at most 3.5 mmole/kg, more preferably at most 3 mmole/kg of catalyst. In this embodiment, the total quantity of the first co-promoter and the second co-promoter may preferably be at least 0.1 mmole/kg, more preferably at least 0.5 mmole/kg, most preferably at least 1 mmole/kg of the catalyst.

The catalyst may preferably further comprise a further element deposited on the carrier. Eligible further elements may be one or more of nitrogen, fluorine, alkali metals, alkaline earth metals, titanium, hafnium, zirconium, vanadium, thallium, thorium, tantalum, niobium, gallium and germanium and mixtures thereof. Preferably, the alkali metals are selected from lithium, sodium and/or cesium. Preferably, the alkaline earth metals are selected from calcium, magnesium and barium. Preferably, the further element may be present in the catalyst in a total quantity of from 0.01 to 500 mmole/kg, more preferably from 0.5 to 100 mmole/kg, calculated as the total quantity of the element relative to the weight of the catalyst. The further element may be provided in any form. For example, salts or hydroxides of an alkali metal or an alkaline earth metal are suitable. For example, lithium compounds may be lithium hydroxide or lithium nitrate.

In an embodiment, the catalyst may comprise cesium as a further element in a quantity of more than 3.5 mmole/kg, in particular at least 3.6 mmole/kg, more in particular at least 3.8 mmole/kg, calculated as the total quantity of the element relative to the weight of the catalyst. In this embodiment, the catalyst may comprise cesium in a quantity of at most 15 mmole/kg, in particular at most 10 mmole/kg, calculated as the total quantity of the element relative to the weight of the catalyst As used herein, unless otherwise specified, the quantity of alkali metal present in the catalyst and the quantity of water leachable components present in the carrier are deemed to be the quantity insofar as it can be extracted from the catalyst or carrier with de-ionized water at 100° C. The extraction method involves extracting a 10-gram sample of the catalyst or carrier three times by heating it in 20 ml portions of de-ionized water for 5 minutes at 100° C. and determining in the combined extracts the relevant metals by using a known method, for example atomic absorption spectroscopy.

As used herein, unless otherwise specified, the quantity of alkaline earth metal present in the catalyst and the quantity of acid leachable components present in the carrier are deemed to be the quantity insofar as it can be extracted from the catalyst or carrier with 10% w nitric acid in de-ionized water at 100° C. The extraction method involves extracting a 10-gram sample of the catalyst or carrier by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

Ethylene oxide produced may be recovered from the product mix by using methods known in the art, for example by absorbing ethylene oxide from a reactor outlet stream in water and optionally recovering ethylene oxide from the aqueous solution by distillation. At least a portion of the aqueous solution containing ethylene oxide may be applied in a subsequent process for converting ethylene oxide into a 1,2-diol, a 1,2-diol ether, a 1,2-carbonate, or an alkanolamine, in particular ethylene glycol, ethylene glycol ethers, ethylene carbonate, or alkanol amines.

Ethylene oxide produced in the epoxidation process may be converted into a 1,2-diol, a 1,2-diol ether, a 1,2-carbonate, or an alkanolamine. As this invention leads to a more attractive process for the production of ethylene oxide, it concurrently leads to a more attractive process which comprises producing ethylene oxide in accordance with the invention and the subsequent use of the obtained ethylene oxide in the manufacture of the 1,2-diol, 1,2-diol ether, 1,2-carbonate, and/or alkanolamine.

The conversion into the 1,2-diol (i.e., ethylene glycol) or the 1,2-diol ether (i.e., ethylene glycol ethers) may comprise, for example, reacting ethylene oxide with water, suitably using an acidic or a basic catalyst. For example, for making predominantly the 1,2-diol and less 1,2-diol ether, ethylene oxide may be reacted with a ten fold molar excess of water, in a liquid phase reaction in presence of an acid catalyst, e.g. 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. The presence of such a large quantity of water may favor the selective formation of 1,2-diol and may function as a sink for the reaction exotherm, helping control the reaction temperature. If the proportion of water is lowered, the proportion of 1,2-diol ethers in the reaction mixture is increased. Alternative 1,2-diol ethers may be prepared by converting ethylene oxide with an alcohol, in particular a primary alcohol, such as methanol or ethanol, by replacing at least a portion of the water by the alcohol.

Ethylene oxide may be converted into the corresponding 1,2-carbonate by reacting ethylene oxide with carbon dioxide. If desired, ethylene glycol may be prepared by subsequently reacting the 1,2-carbonate with water or an alcohol to form the glycol. For applicable methods, reference is made to U.S. Pat. No 6,080,897, which is incorporated herein by reference.

The conversion into the alkanolamine may comprise, for example, reacting ethylene oxide with ammonia. Anhydrous ammonia is typically used to favor the production of monoalkanolamine. For methods applicable in the conversion of ethylene oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The 1,2-carbonates may be used as a diluent, in particular as a solvent. The alkanolamine may be used, for example, in the treating ("sweetening") of natural gas.

What is claimed is:

1. A process for the start-up of an ethylene epoxidation process comprising:
   (a) contacting a catalyst bed comprising a high selectivity epoxidation catalyst with a feed comprising ethylene, oxygen and an organic chloride in a quantity that is above the optimum quantity used during the initial period of normal ethylene oxide production for a period of time until an increase of at least $1 \times 10^{-5}$ mole-% of vinyl chloride (calculated as the moles of vinyl chloride relative to the total gas mixture) is detected in a reactor outlet gas or a recycle gas loop; and
   (b) subsequently adjusting the quantity of organic chloride in the feed to a value sufficient to produce ethylene oxide at an optimum selectivity.

2. A process for the start-up of an ethylene epoxidation process as claimed in claim 1 wherein an increase of at least $2 \times 10^{-5}$ mole-% of vinyl chloride is detected in the reactor outlet gas or the recycle gas loop before adjusting the quantity of organic chloride in the feed.

3. A process for the start-up of an ethylene epoxidation process as claimed in claim 1 wherein the increase of vinyl chloride in the reactor outlet gas or the recycle gas loop is at most $1 \times 10^{-4}$ mole-%, (calculated as the moles of vinyl chloride relative to the total gas mixture).

4. A process for the start-up of an ethylene epoxidation process as claimed in claim 1 wherein the increase of vinyl chloride in the reactor outlet gas or the recycle gas loop is at most $7.5 \times 10^{-5}$ mole-%, (calculated as the moles of vinyl chloride relative to the total gas mixture).

5. A process for the start-up of an ethylene epoxidation process as claimed in claim 1 wherein the quantity of organic chloride contacted with the catalyst in step (a) is in the range of from 1 to 12 millimolar (mmolar) equivalent of chloride per kilogram of catalyst.

6. A process for the start-up of an ethylene epoxidation process as claimed in claim 1 wherein the quantity of the organic chloride contacted with the catalyst is at most 6 mmolar equivalent/kg catalyst.

7. A process for the start-up of an ethylene epoxidation process as claimed in claim 1 wherein the quantity of the organic chloride contacted with the catalyst is at most 5 mmolar equivalent/kg catalyst.

8. A process for the start-up of an ethylene epoxidation process as claimed in claim 1 wherein the quantity of the organic chloride in the feed in step (a) is at least $1.5 \times 10^{-4}$ mole-%, calculated as moles of chloride, relative to the total feed.

9. A process for the start-up of an ethylene epoxidation process as claimed in claim 1 wherein the quantity of the organic chloride in the feed in step (a) is at least $2 \times 10^{-4}$ mole-%, calculated as moles of chloride, relative to the total feed.

10. A process for the start-up of an ethylene epoxidation process as claimed in claim 1 wherein the quantity of the organic chloride in step (a) is at most 0.1 mole-%, calculated as moles of chloride, relative to the total feed.

11. A process for the start-up of an ethylene epoxidation process as claimed in claim 1 wherein the quantity of the organic chloride in step (a) is at most 0.001 mole-%, calculated as moles of chloride, relative to the total feed.

12. A process for the start-up of an ethylene epoxidation process as claimed in claim 1 further comprising an intermediate step after step (a) of contacting the catalyst with a feed comprising the ethylene, oxygen and the organic chloride, wherein the quantity of organic chloride in the feed is at most 80% of the quantity of organic chloride in the feed in step (a).

13. A process for the start-up of an ethylene epoxidation process as claimed in claim 1 wherein the organic chloride is fed to the catalyst bed in step (a) for a period of time ranging from 1 to 15 hours.

14. A process for the start-up of an ethylene epoxidation process as claimed in claim 1 wherein the organic chloride is fed to the catalyst bed in step (a) for a period of time ranging from 2.5 to 8 hours.

\* \* \* \* \*